United States Patent

Guichet

Patent Number: 5,431,564
Date of Patent: Jul. 11, 1995

[54] DENTAL ARTICULATOR AND INSPECTION AND CALIBRATION SYSTEM

[76] Inventor: Niles F. Guichet, 100 Strada Pl., Anaheim, Calif. 92807

[21] Appl. No.: 119,393

[22] Filed: Sep. 13, 1993

[51] Int. Cl.⁶ .................................................. A61C 11/00
[52] U.S. Cl. .................................................. 433/56; 433/55
[58] Field of Search .................. 433/55, 56, 57, 58, 433/59, 60, 64, 72

[56] References Cited

U.S. PATENT DOCUMENTS

| | | | |
|---|---|---|---|
| 3,343,264 | 9/1967 | Guichet | 433/56 |
| 3,350,782 | 11/1967 | Guichet | 433/56 X |
| 3,708,882 | 1/1973 | Guichet | 433/56 |
| 3,750,289 | 8/1973 | Guichet | 433/56 |
| 3,769,708 | 11/1973 | Guichet | 433/56 X |
| 3,808,688 | 5/1974 | Guichet | 433/55 |
| 5,055,041 | 10/1991 | Eckland | 433/56 |

*Primary Examiner*—Gene Mancene
*Assistant Examiner*—Nicholas D. Lucchesi
*Attorney, Agent, or Firm*—Plante Strauss

[57] ABSTRACT

There is disclosed a calibration device for the inspection and precise setting of dental articulators which includes a stage member that is removably secured to the articulator lower frame and an scope gauge member that is removably secured to the upper frame of the articulator. A pair of position sensing indicators having sensing probes which are carried at the opposite sides of the stage member and are mechanically coupled by levers to contact points on the scope member which are located on the right and left axes of rotation of the articulator members. This permits the indicators to read, directly, relative vertical movements of the opposite sides of the articulator without being influenced by adjustments made at the opposite sides of the articulator. The inspection device includes ocular magnifiers including reticle and target indicium which cooperate to provide a vernier scale registering relative X-Y positions of the stage and gauge inspection members. The invention also includes magnetically secured dental cast and appliance mounting plates having removable magnets and metal plugs.

24 Claims, 7 Drawing Sheets

DENTAL ARTICULATOR AND INSPECTION AND CALIBRATION SYSTEM

BACKGROUND OF THE INVENTION

1. Field of Invention

This invention relates to improvements in dental articulators and, in particular to an inspection and calibration system for a dental articulator.

2. Brief Statement of the Prior Art

In the development of dental prostheses such as crowns, bridges, inlays and dentures, the dentist mounts casts of the dental structures in cast relating devices which range from simple, inexpensive devices which reproduce only the opening and closing movements of the jaw to very complex, fully adjustable dental articulators, such as those described in my prior U.S. Pat. Nos. 3,343,264; 3,590,487; and 4,024,640. The articulators disclosed in those patents are arcon type with adjustable guides which allow the articulator to reproduce the movements of the human jaw, e.g., by permitting a controlled degree of lateral, vertical and posterior-anterior translation of the condyles during lateral rotation of the articulator members. The fully adjustable articulators are approximately six to ten times more costly than the simple devices.

Casts of the patient's dental structures are mounted in the articulating devices by mounting plates which are secured to the upper and lower members of the articulator with threaded screw attachments which are cumbersome to use. An attempt has been made to improve the efficiency of mounting casts by use of cast aluminum plates with permanent magnets and steel armatures, however, the magnetic attraction of these plates to the mounting armature is not adjustable and frequently is excessive.

It is a general practice of dentists to leave casts mounted in a dental articulator until completion of the case which, in extensive cases, may take several months. This practice has been referred to as the "one instrument system". During this time, the articulator is used only a matter of hours to replicate the movements of the human jaw during fabrication of the dental occlusion. Typically, the articulator is unavailable for use on other cases for many hours, days and sometimes weeks, particularly in extensive cases, awaiting other stages of the fabrication processes or the patient's healing processes, or completion of other treatments. The consequence is that the dentist must have many articulators; a very costly investment.

The one instrument system in which the case remains in one instrument during the entire fabrication process leads to my inventions disclosed in my U.S. Pat. Nos. 3,750,289 and 3,808,688. In these patents, I describe an inspection means for calibrating the vertical and horizontal adjustments of the articulator.

in 1972, I introduced a two instrument system which used a device for calibrating articulators in both the vertical and horizontal planes and an inspection gauge to align the bows of a family of articulators so that casts could be transferred between the articulators. My objective was to allow the casts to be mounted in simple inexpensive articulators for certain stages of the fabrication process and only mount the casts in fully adjustable articulators for limited periods of time when the fully adjustable capabilities of those articulators were needed. It was the objective of this invention, called a "Two Instrument System", to allow the casts to be transported between work stations independently of the articulator and to use an articulator selected at each work station for the particular work to be done at that point in time. This was intended to reduce the number of articulators a dentist needed by avoiding tying up an expensive articulator for the total time while the restoration was being fabricated. This "Two Instrument System" did not achieve commercial success because it was very difficult and time consuming to align the bows of the articulator. Although I provided an inspection gage for this purpose, difficulties were experienced with this gage which were not entirely overcome. One problem was that the bows were aligned with finger pressure used to slide the upper member of the instrument against the lower member while attempting to align the bows precisely within a tolerance of a thousand of an inch. Frequently, tightening the lock screws would push the instrument out of specification. Furthermore, the prior inspection device described in my U.S. Pat. No. 3,808,688 was inefficient because the dial indicators of that device, which sensed the right and left vertical separations of the bows of the instrument, were responsive to adjustments on both sides of the articulator, whereby the left side indicator would respond to adjustment on the right side of the articulator. This was referred to as "run out" and greatly complicated calibration of the articulator since the dentist or technician was required to go back and forth in repeated adjustments five or six times to achieve a null reading on both sides of the articulator. The result was that few users developed the necessary skill to calibrate an articulator quickly, and the system did not receive broad acceptance.

OBJECTIVES OF THE INVENTION

It is an objective of this invention to provide a means for securing casts to the bows of the articulator by magnetic attraction to eliminate the inefficiencies of using screws.

It is also an objective of this invention to provide a means to control the degree of attraction of the magnets to the bows of the articulator to satisfy varying customer needs.

It is also another objective of this invention to provide a magnetic mounting system with economical plastic and durable metal mounting plates.

It is another objective of this invention to use magnet cassettes to permit removal and transfer of the magnets between plastic and metal mounting plates by the user.

It is a further objective of this invention to provide an inspection means which can allow the bows of the articulator to be calibrated to within one ten thousandths of an inch (0.0001") on each of the x, y and z axes.

It is a further objective of this invention to provide a positioning fixture which will allow the maxillary (upper) member of the mounting plate system to be adjusted in the horizontal plane along the X and Y axis to within one ten thousands inch (0.0001 inch) by means of three cam mechanisms.

It is a still further objective of this invention to provide a system in which vertical adjustment of one condylar element of the articulator will have little or no reciprocal affect on the vertical reading of the indicator at the opposite side of the articulator.

It is an additional objective of this invention to provide for back lighting of the targets viewed by the microscopes in calibrating the horizontal position of the bows of the articulator.

It is another objective of this invention to provide a calibration system which allows adequate adjustment capability in the horizontal plane to bring the instruments into specification by the user.

It is another objective of this invention to provide a calibrating scope and stage system having cooperative reticle and target indicium, which together provide for vernier calibration to within 0.0001 inch of the centric reference position.

BRIEF DESCRIPTION OF THE INVENTION

The invention comprises a device for the precision and inspection setting of dental articulators of widely varied complexity, from those having simple hinges to fully adjustable arcon type dental articulators. The inspection device comprises a stage member that is removably secured to the articulator lower frame and an scope gauge member that is removably secured to the upper frame of the articulator. A pair of position sensing indicators having sensing probes which are carried at the opposite sides of the stage member and are mechanically coupled by pivotal levers also carried on the stage member and which extend from operative contact with the sensing probes of the indicators to a contact point on the gauge member which is located on the respective right or left axis of rotation of the articulator members. This permits the indicators to read, directly, relative vertical movements of on each side of the articulator without being influenced by vertical adjustments made at the opposite sides of the articulator. The inspection device includes ocular magnification means such as used in a microscope with a tubular housing objective and eyepiece lenses and including reticle and target indicia which cooperate to provide a vernier scale registering relative X-Y positions of the stage and gauge inspection members. The invention also includes dental cast and appliance mounting plates which include a pair of opposed and centering plates which also include magnets for interlocking the plates. The magnets are contained in removable canisters so that they can be incorporated in inexpensive plates formed of plastics by injection molding.

BRIEF DESCRIPTION OF THE DRAWINGS

The invention will be described with reference to the figures of which.

DESCRIPTION OF PREFERRED EMBODIMENTS

This invention comprises a device for precision inspection and setting of dental articulators, and is useful with all articulators, regardless of their complexity. Although it can be used with very simple articulators, it is illustrated in this application as applied to the inspection and setting of a fully adjustable arcon-type dental articulator, which is shown in FIG. 1.

The articulator has a lower frame member 10 that has a rear bow formed by a crossbar 12 that is supported on a pair of opposite, generally upright legs 14 and 16. The cross bar 12 slidably supports a pair of right and left condyles which are carried on blocks 18 that are slidably engaged in a keyway 20 and that are fixedly secured at a selected position by an adjustment knob 22.

Figures 1, 2:
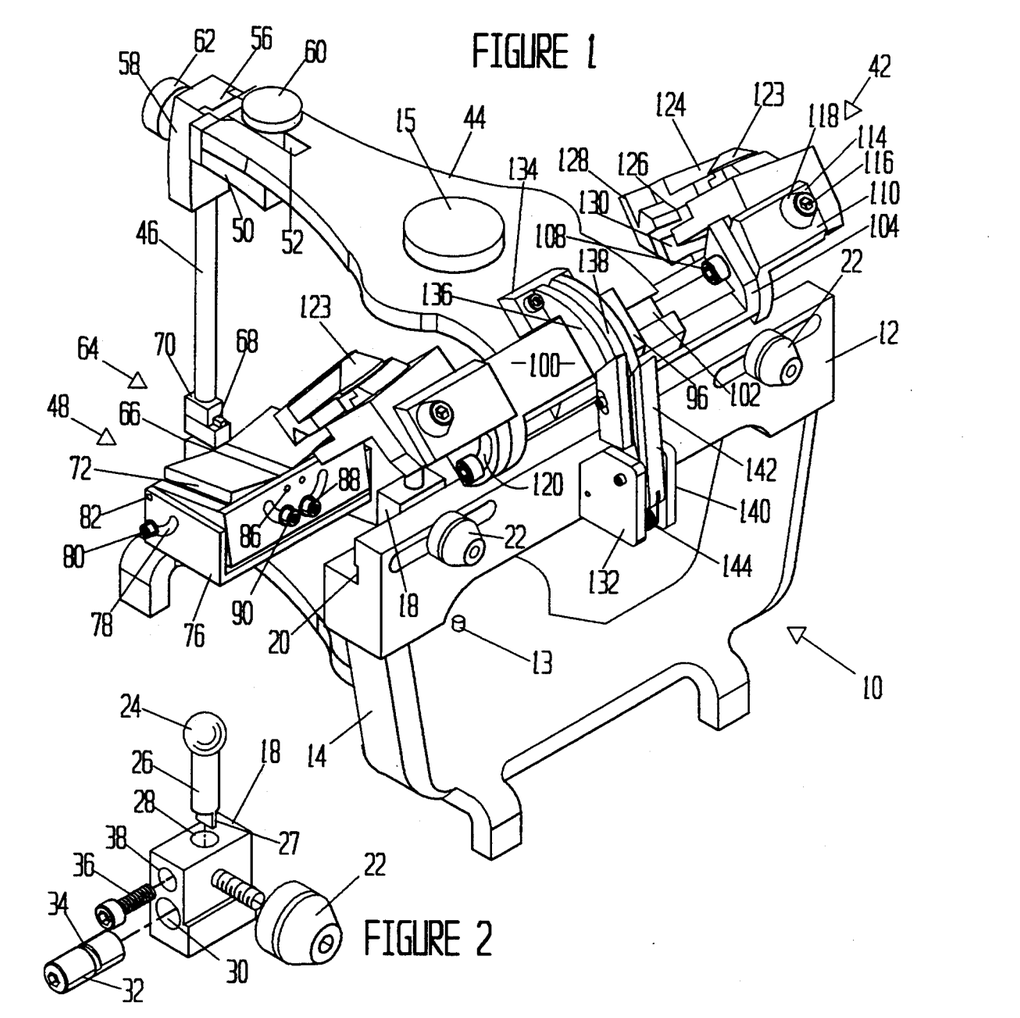
FIG. 1 illustrates a fully adjustable dental articulator.
FIG. 2 is an exploded illustration of the condylar mount used in the articulator of FIG. 1.

As shown in the exploded view of FIG. 2, the condyles 24 are supported on the upper ends of condyle shafts 26 which are slidably received in bores 28 in the top surface of the blocks 18. The vertical positions of the condyles are fixedly adjustable, and for this purpose, blocks 18 have orthogonal bores 30 which intersect the bores 28 and cam shafts 32 are rotatably received in the bores 30. Each shaft 32 has a helical groove 34 which is centered beneath bore 30, and the end of each of the condyle shafts 26 has a blade cam follower 27 which rides in the groove 34, so that rotation of the cam shaft 32 raises and lowers the condyle 24. The blade cam follower 27 seats in groove 34 and thereby prevents rotation of the condyle 24. The vertical position of the condyle 24 is fixedly secured by a set screw 36 which is received in an internally threaded bore 38 in block 18 and which project into binding engagement with the condyle shaft 26.

The condyles 24 are received against the under surface 40 of the fully adjustable condylar guides 42 which are laterally disposed on the upper articulator frame member 44.

At their anterior ends, the articulator frames 10 and 44 are supported by an incisal pin 46 and incisal table 48. The pin 46 is supported by an adjustable pin bracket 50 that is slidably supported in a central slot 52 in the forward end of the tongue 54 of the upper frame member 44 and is vertically adjustable by a tongue and groove joint 56 with the pin support block 58. Adjustment knobs 60 and 62 fixedly secure the selected settings of the fore and aft and vertical settings of the incisal pin 46. The incisal pin 46 has a foot 64 that is slidably secured by a tongue and groove joint 68 to bracket 70 which is permanently attached to the end of the pin 46. The fore and aft position of the foot 64 on bracket 70 is fixedly secured by a set screw (not shown) in the bracket 70. The lower edge of the foot 64 rests on an incisal support pad 66 and can be guided posteriorly and laterally on the adjustable wings 72 and 74 of the incisal table 48.

The incisal table 48 is supported on the lower frame member 10 by a support bracket 76 which is secured to the anterior end of the lower articulator frame member 10. This bracket 76 has, on each of its opposite sides, an arcuate slot 78 on each side which receives a set screw 80 that is received in an internally threaded bore in the side of the incisal table 48. The table 48 is pivotally mounted on pins 82 at the opposite upper anterior corners of the support bracket 76, so that the inclination of the upper surface of the table can be adjusted and fixedly secured.

The incisal table 76 has a pair of wings 72 and 74 which are pivotally mounted at opposite sides of a central guide 84. Each of the wings 72 and 74 is pivotally mounted in the table assembly on a pivot pin 86 and the rear side of the table 48 has a pair of arcuate slots 88 that receive set screws 90 to fixedly secure the angular setting of each of the wings 72 and 74.

The upper frame member 44 and the lower frame member 10 have cast mounting facilities which, in the prior art articulator comprises a screw which extends through its respective tongue for threaded engagement in a mounting plate for a dental cast.

At the rear of the articulator, the upper frame 44 and lower frame 10 are hinged together in a fully adjustable condylar joint. As previously mentioned, the lower frame 10 supports left and right condyles 24 on shafts 26 which are carried by the slidable condyle blocks 18. The upper frame member 44 rests on the condyles 24 with fully adjustable fossa assemblies 42. The upper frame member distally supports a dovetail guide 96 which has dovetail slots on its upper and lower surfaces. The left dovetail slide 100 is slidably received in the top dovetail guide and a right dovetail slide 102 is slidably received in the lower dovetail guide 96. Each dovetail slide laterally supports an orthogonal flange 104 which has a through aperture that receives a mounting screw 108 which threadably engages in an internally threaded tap in a respective fossa bracket 110. Each fossa bracket 110 is of right angle configuration and has a through aperture in its outer, upper corner 114 which receives a mounting screw 116 and a cone washer 118 for the pivotal mounting of a fossa frame. The fossa bracket 110 has an arcuate slot 120 which receives a set screw 122 that extends into a threaded tap in the flange 104 of the dovetail slide, thereby permitting fixed adjustability of the angular position of the fossa bracket 110 about its mounting screw. The fossa frame has a fully adjustable posterior wall (not shown) which has a threaded tap that engages the end of the set screw 123. This permits rotation of the posterior wall about the axis of the set screw 123. The set screw 123 also pivotally secures the medial wall index bracket 124 which can be pivoted about the axis of the screw 123 and can be fixedly secured in any position by tightening of the screw. The medial wall bracket 124 has a dovetail slot 126 that slidably receives the medial wall support bracket 128. The forward upper rim on the medial wall index bracket has a through slot (not shown) which receives set screws that extend into threaded taps in the medial wall support bracket whereby the position of the sliding medial wall support bracket can be fixedly secured to the medial wall index bracket. The medial wall support bracket has an orthogonal medial wall support arm 130 to which is secured the medial wall (not shown). Together, these adjustable walls and guides of the fossa assembly provide complete adjustability of the fossa/condylar joint of the articulator.

The articulator also has, at its posterior, a centric lock 132. The centric lock 132 comprises a centric latch guide 134 fixedly mounted to the top surface of the upper frame member 44 and this guide has an arcuate flange 136 with a longitudinal V-slot 138. The lower frame member 10 centrally carries a latch mechanism which is attached to the lower cross bar 12 of the articulator by a latch support bracket 140 that pivotally supports a latch key 142 which has a knife edge that engages in the V-slot 138 of the centric latch guide 134. The latch support bracket 140 also supports a coil spring 144 to provide a resilient bias of the latch key 142 into the V-slot 138 of the centric latch guide.

Figure 3:
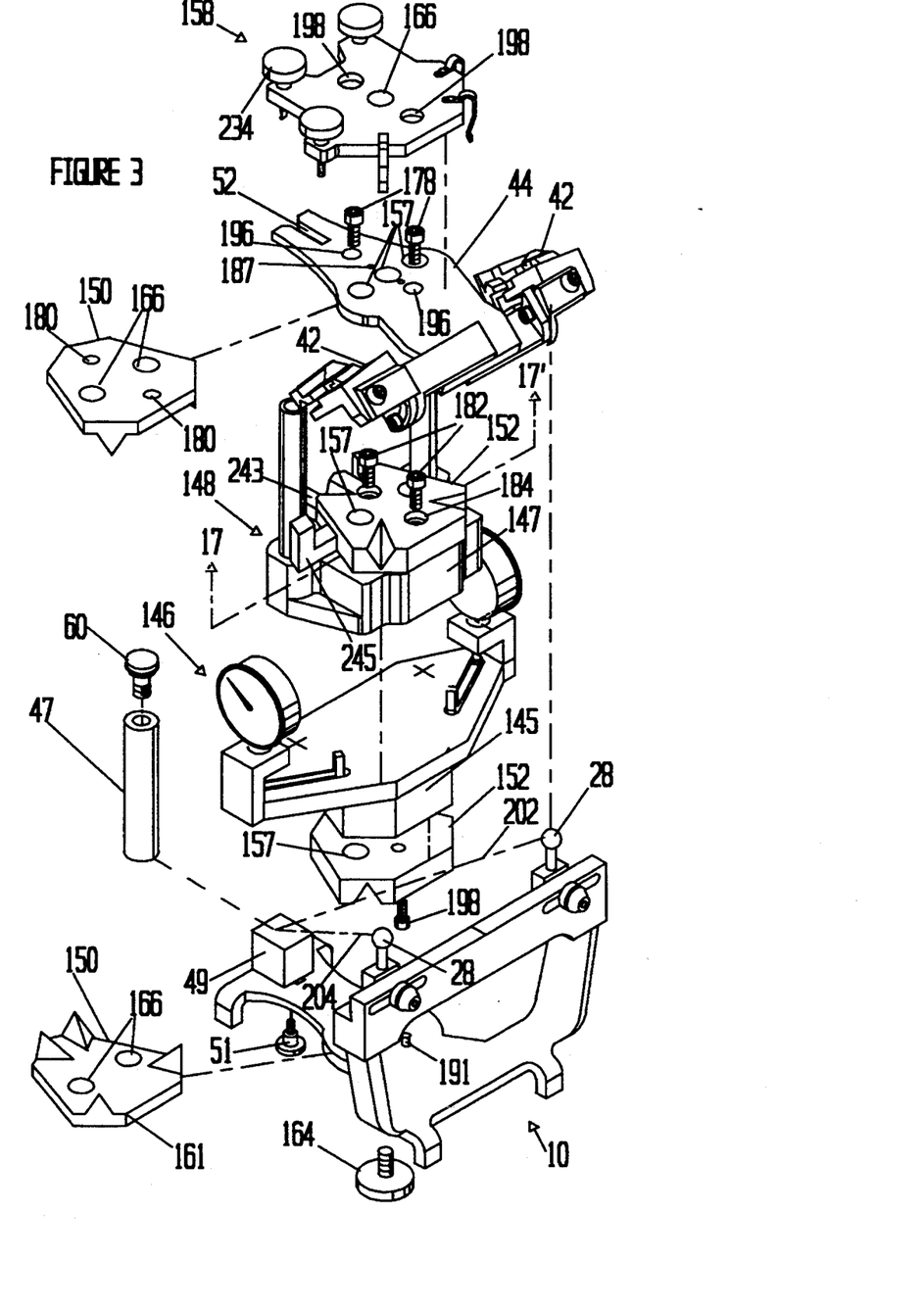
FIG. 3 is an exploded view of the cast mounting system, positioning fixture, stage and scope members of the articulator calibration system of this invention as installed in the articulator shown in FIG. 1.
Figures 4, 5, 6, 7:
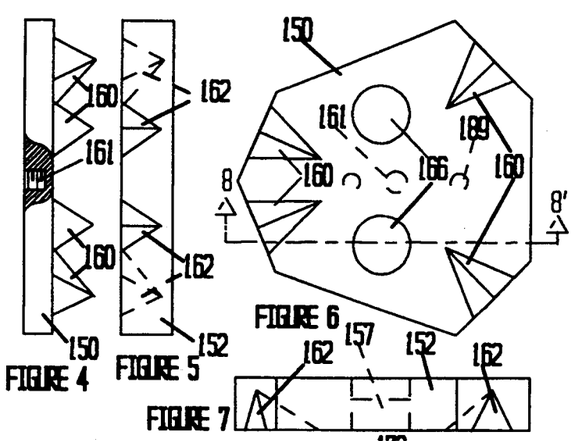
FIGS. 4–8 are front, top and side illustrations of the cast mounting plates of the invention.

Referring now to FIG. 3, there is illustrated in exploded view the articulator substantially as described and illustrated in FIG. 1, with the calibration apparatus of the invention. The articulator is altered from that shown in FIGS. 1 and 2, by the substitution of an incisal gage pin 47 for the incisal pin 46 shown in FIG. 1, and incisal rest 49 for the incisal table 48, also shown in FIG. 1. This substitution is made by removing the incisal table 48 and the pin bracket 50 with its dependent incisal pin 46, and inserting the gage pin 47. The gage pin 47 has a threaded bore in its upper end which receives lock screw 60 that is received in central slot 52 in the forward end of the upper frame member 44. The incisal rest 49 has a bottom flange(not shown) which is received in the central slot in the forward end of the lower frame member 10. A lock screw 51 is threaded into a bore in the underside of the incisal rest 49 to secure the rest 49 to the lower frame member 10. The gage pin 47 and the incisal rest 49 are of precise heights and serve to separate the anterior ends of the upper and lower frame members 10 and 44 at a precise, predetermined vertical distance.

The lower articulator frame 10 and the upper articulator frame 44 are shown separated by a sufficient distance to interpose the stage 146 and the scope 148 of the calibration apparatus. Also shown to the left of the articulator and calibration apparatus are the mounting base plates 150 which are adapted for use in mounting the calibration apparatus to the articulator. At the very top of the illustration is a positioning fixture 158 which is used to obtain a precise x-y orientation of the mounting base plate 150 that is fixedly secured to the upper frame member 44 relative to the mounting base plate 150 which is fixedly secured to the lower frame member 10 of the articulator.

Figure 25:
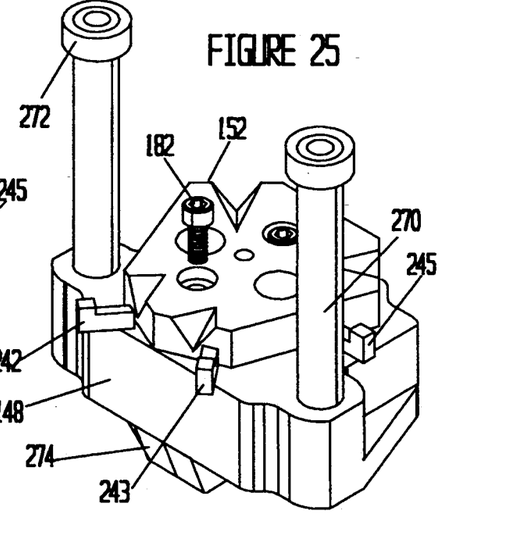
Figure 26:
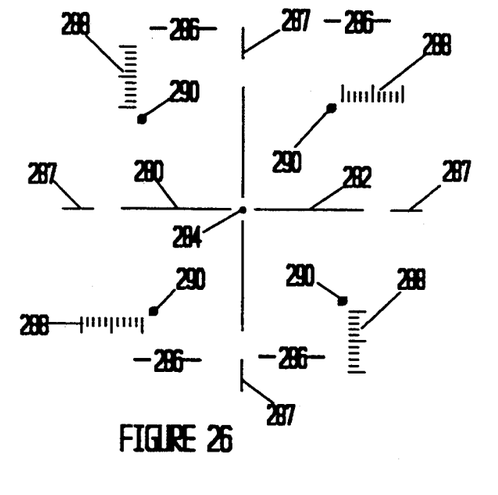
FIGS. 26–28 illustrate the reticle, the target and the overlay of the reticle and target used with the base and scope of the calibration fixture.
Figure 27:
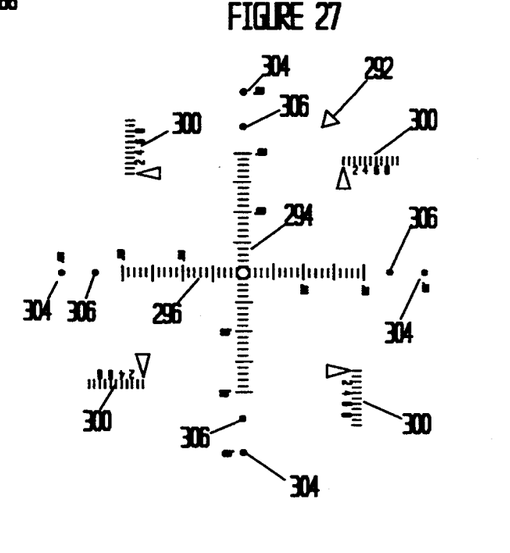
Figure 28:
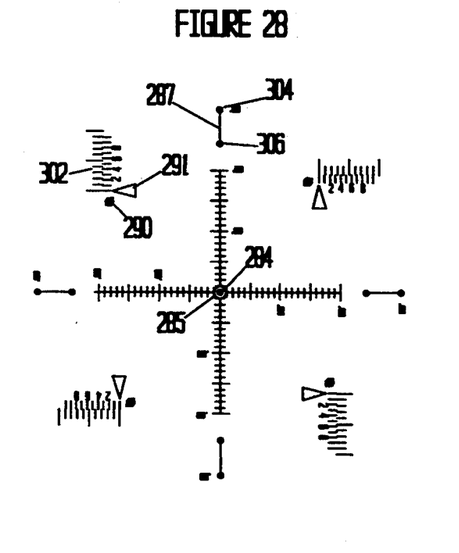

The base mounting plate 150 and appliance mounting plate 152 are illustrated and described in greater detail with reference to FIGS. 4 through 12. The positioning fixture 158 is described in detail and illustrated in FIGS. 13 through 17. The calibration stage 146 is described and illustrated in greater detail in FIGS. 18 through 21. The scope member 148 of the calibration apparatus is described and illustrated in FIGS. 22 through 25, and the reticle of the scope member 148 and target of the stage member 146 are illustrated in FIGS. 26–28.

Referring again to FIG. 3, the lower frame member 10 of the articulator supports a mounting base plate 150 of the mounting plates of the invention, which is secured to the frame member 10 with screw 164 which engages a central, threaded bore 161 (see FIGS. 4 and 6) in plate 150. The plate 150 is oriented on the frame by dowel pins 191 which seat in bores 189 (see FIG. 3) in plate 150.

As shown in FIGS. 4–11, each of the mounting plates, 150 and 152, has a heptagon shape and the plates are used in pairs with a base plate 150 and its mating appliance plate 152 having opposed surfaces with interlocking V-shaped keys 160 and V-shaped grooves 162. The plates are symmetrical about their longitudinal axis and each plate has a pair of apertures in which are received magnetic elements. The base plate 150 has a centrally located, internally threaded bore 161 to receive a mounting screw (see FIG. 3). The lower base plate 150 also has a pair of small diameter bores 189 (see FIG. 6) to receive dowel pins that precisely orient the plate on the lower frame 10 of the articulator. The bores 161 and 189 do not extend entirely through the plate 150, thereby presenting a smooth upper surface for plaster; see FIG. 12, described hereinafter. The base plate 150 receives a pair of removable cassettes 166 (see FIGS. 8 and 9), each of which contains a permanent cylindrical magnet 168. The cassettes fit snugly in receiving apertures 172, which have enlarged counterbores to receive the annular rims 174 of the cassettes 166. The assembly also includes one or more washer spacers 170 which are used to provide a variable adjustment in the depth of the cassette 166 in the receiving aperture 172, thereby permitting a variation in the air gap between the magnets of the plates and ferrous plugs 157 which are placed in the mating plate, so the user can adjust the strength of the magnetic attraction between the mating plates 150 and 152. The appliance plate 152 of the pair of mounting plates has a pair of ferrous metal, preferably steel, plugs 157 which are attracted to the magnets of the cassettes 166. In this manner, plates 150 and 152 can be formed of any metal, e.g., aluminum and its alloys, or can be inexpensive plastic plates prepared by injected molding.

Figures 8, 9, 10, 11, 12:
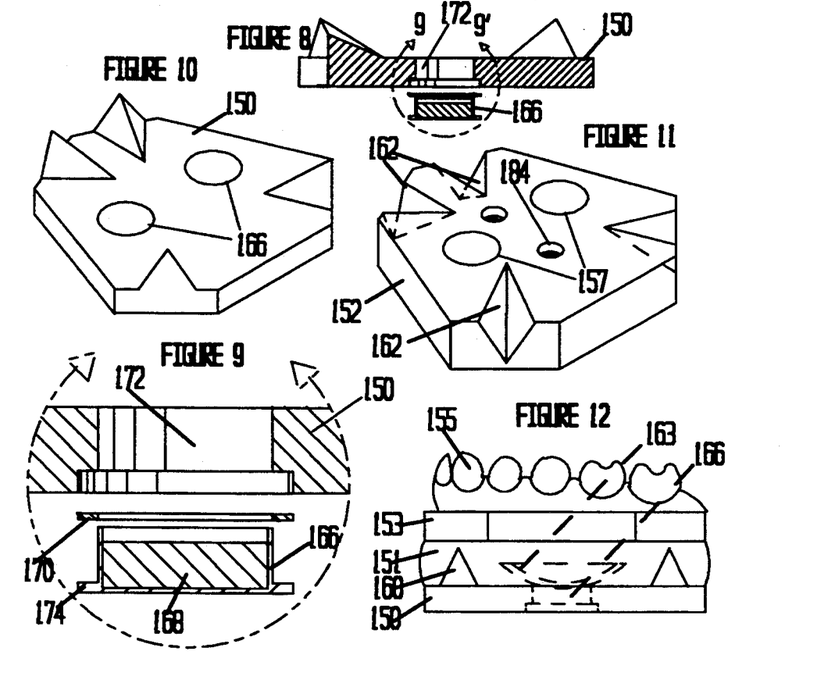
FIG. 9 is an enlarged view of the area within line 9–9' of FIG. 8.
FIGS. 10 and 11 are perspective views of the base and appliance plates of the cast mounting plates of the invention.
FIG. 12 illustrates the mounting of a dental cast with the cast mounting plates of the invention.
Figure 13:
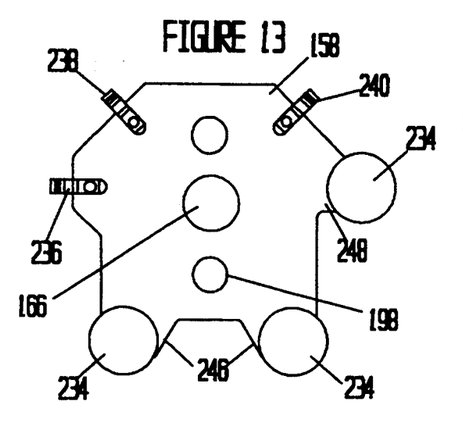
FIGS. 13–16 are top, side, front and perspective illustrations of the positioning fixture of the invention.
Figure 14:
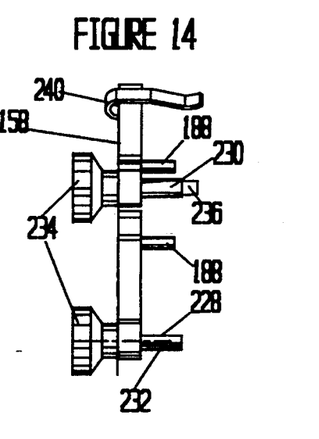

The keys 160 are upright, right-angle tetrahedrons conforming to the shapes of the triangular grooves 162 in the edges of the appliance plate 152, such that when the plates are stacked together, they automatically index to a precise fit in the X-Y axis.

As shown in FIG. 12, the base plates are used to mount and orient dental casts in an articulator. The dental cast 153 with cast teeth 155 is secured with a layer 151 of plaster to the plate 150. For this purpose, steel keepers 163 having the form of dished plates are embedded in the plaster layer 151. The keys 160 of plate 152 form recesses so that the dental cast 153 can be removed and replaced on the plate 150.

Referring again to FIG. 3, the base plate 150 which is attached to the upper frame member 44 of the articulator is shown in the orientation that it will assume when attached to the upper articulator frame by set screws 178 which engage threaded bores 180 in plate 150. Bores 180 extend into but not through plate 150. The screws 178 are received in oversized bores 196 in the upper frame member 44, to permit lateral and fore and aft positioning movement of the upper base plate 150 and its dependent scope member 148 relative to the upper articulator frame member 44. Access to screws 178 is provided by through bores 198 in the positioning fixture.

The female plate 152 of the upper scope subassembly is attached to the body 147 of the scope member 148 by set screws 182 which extend through apertures 184 in the plate 152 and into threaded bores in the scope member body 147. The female plate 152 of the stage member subassembly is secured to the undersurface of the body 145 of the calibration stage 146 by attachment screws 198 which extend into threaded bores in body 145.

The upper and lower articulator frame members, 44 and 10, rest together on a three point contact that includes the left and right condyles 28 and the incisal pin 46 at the anterior of the incisal table 48. During adjustment of the vertical height of the condyle 28 (see FIG. 2) on the left of the instrument, the upper frame 44 will rotate about the axis shown by the dashed line 202 (see FIG. 3) which is an axis extending from the right condyle 28 to the anterior incisal pin support on incisal rest 49. Similarly, adjustments of the vertical height of the right condyle 28 will cause the upper member to rotate about the axis shown by the dashed line 204 which extends between the left condyle 28 and the anterior incisal pin support on incisal rest 49 (see FIG. 3).

The stage 146 of the calibration apparatus of the invention is shown in FIGS. 18–21. The stage 146 supports at its lateral ends, position indicators, which are conventional dial indicators 206 having position probes 208. Each position probe 208 seats on the end of a lever 210 which is received in a slot 214 in the table 216 of the calibration stage 146. The levers 210 are pivotally mounted in the stage 146 with mounting pins 212. Each lever has, at its opposite end, an upright post 218 that extends into contact with the undersurface of the scope member 148 of the calibration apparatus, on its respective, right or left axis of rotation 202 or 204 (see FIG. 3) of the articulator members.

The indicators provide precise readings of the vertical separations of the right and left sides of the articulator, and the user can quickly and accurately bring the upper and lower frames, 44 and 10, of the articulator into precise vertical alignment by loosening the set screw 36 in the condyle block 18 (see FIG. 2), and rotating the cam shaft 32 to raise or lower the condyle 24 as required to null the reading of the indicator, at which point the set screw 36 is tightened to lock the height of the condyle 24. This can be performed step wise on one side and then the next side of the articulator. Since the indicators register vertical separation along the axes of rotation (202 and 204 of FIG. 3) of the articulator frames, adjustment on one side of the articulator will not affect the vertical separation on the opposite side. Thus the user can accurately set the vertical positions of the condyles 24 in only one adjustment for each side, without the need to readjust the settings after changes are made to the vertical settings on the opposite side.

The lateral wings of the stage 146 also carry at lateral positions symmetrical about the midline of the stage 146, target indicia 220 which register with reticles that are in the right and left scopes carried by the scope member 148. The target indica are shown and described hereinafter with reference to FIGS. 26–28.

The positioning fixture 158, which is shown in detail by FIGS. 13–17, is secured to the top surface of the upper articulator frame 44 by a centrally located magnet cassette 166 which is attracted to a steel plug 157 (see FIG. 3) in the upper frame member 44. A precise orientation of the positioning fixture 158 to the frame member 44 is achieved by dowel pins 188 on the undersurface of the fixture 158, which seat in bores 187 (see FIG. 3) of the frame member 44. The positioning fixture 158 is a flat planar member which has three lugs; lugs 244 and 246 on its forward edge and lug 248 on one side which have through apertures that receive rotatable shafts 232 (best shown in FIG. 16), on which are carried adjustment knobs 234. The shafts 232 are flatted on one side, to provide three adjustment cams 226, 228 and 230, which are located on the lower ends of shafts 232. Each adjustment cam is opposed to a resilient leaf spring 236, 238 and 240 which extends downwardly from the upper surface of the positioning fixture 158.

Figures 15, 16, 17:
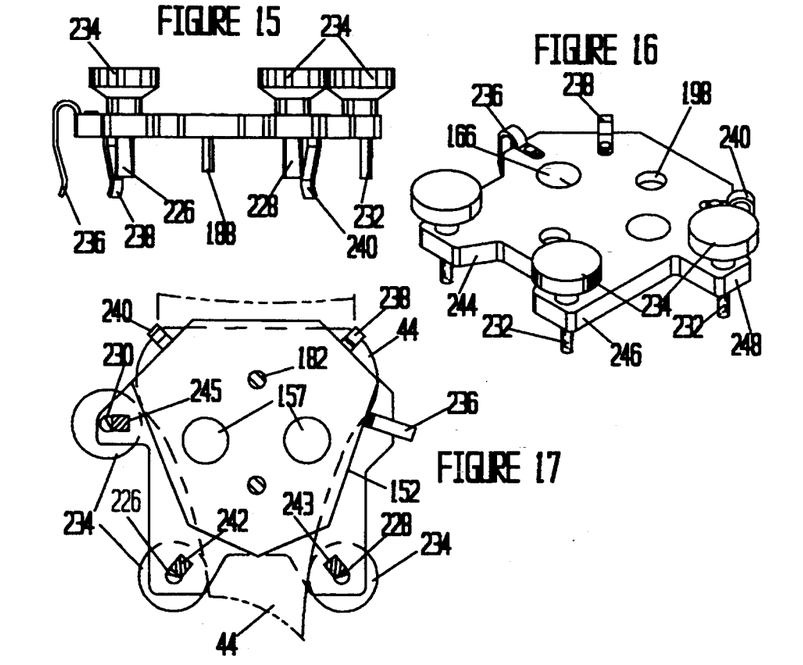
FIG. 17 is an illustration of the underside of the upper frame of a dental articulator with the positioning fixture and cast mounting plates installed.
Figures 18, 19, 20:
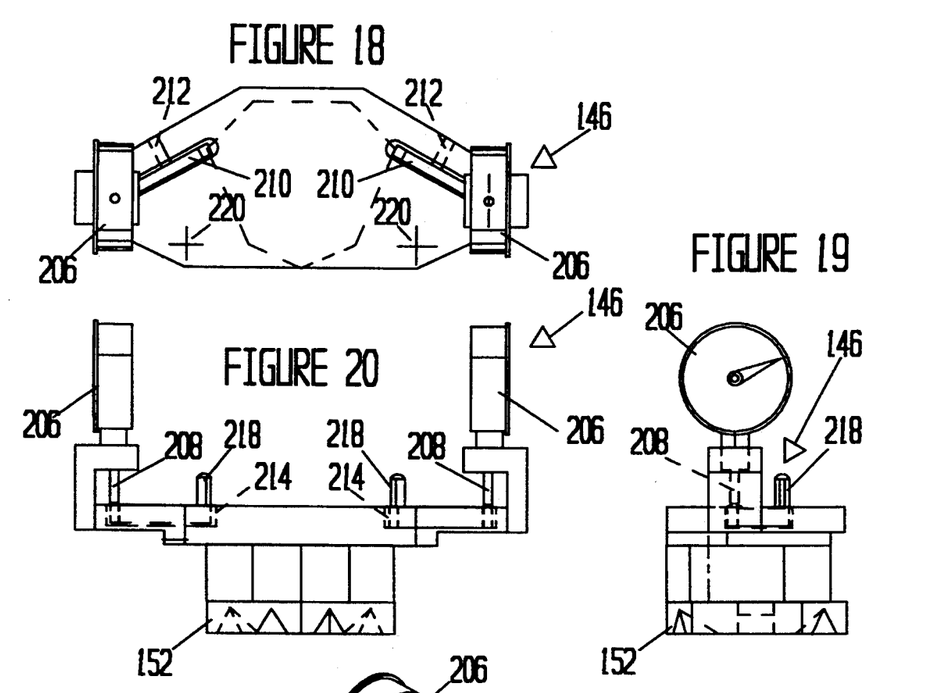
FIGS. 18–21 are top, side, front and perspective illustrations of the stage member of the calibration system of the invention.
Figure 21:
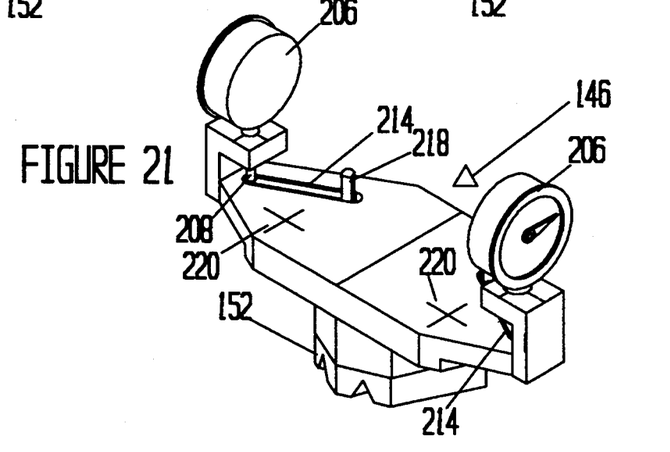
Figure 22:
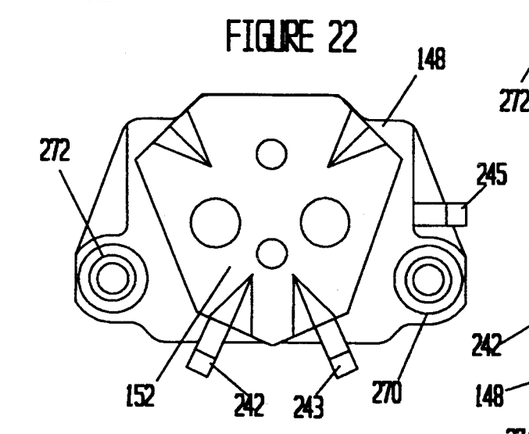
FIGS. 22–25 are top, side, front and perspective illustrations of the scope member of the calibration system of the invention.
Figure 23:
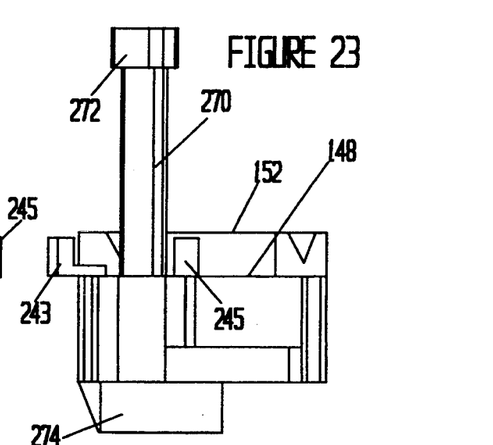
Figure 24:
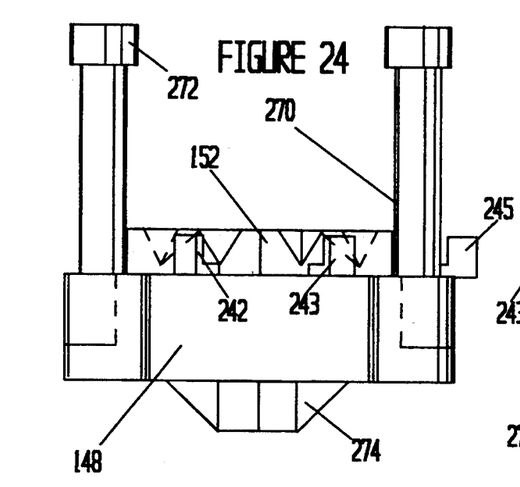

FIG. 17 is a view along line 17-17' of FIG. 3, looking upwardly from the undersurface of appliance plate 152. The scope member body has a pair of lugs 242 and 243 on its front surface which bear against the cams 226 and 228 on the shafts 232 attached to the adjustment knobs 234. The body 147 also has a third lug 245 which bears against cam 230. The lugs 242, 243 and 245 are best shown in FIGS. 24-25.

The springs 236, 238 and 240 hook over the upper frame member 44 and resiliently bear against the sides of plate 152, with each spring biased against a respective cam 226, 228 and 230. This structure permits side to side and fore and aft (x-y) adjustment of the position of the mounting plates 150 and 152 on the frame member 44. Since plate 152 is fixedly secured to the scope member 148 by screws 182, and mechanically indexed and magnetically secured to mounting plate 150, rotation of adjustment knobs 234 displaces the mounting plate 152, scope member 148 and plate 150 in precisely controlled distances and directions.

The scope member 148 is shown in FIGS. 22-25, with the female appliance plate 152 attached to its upper surface by screws 182. The scope member is a flat plate which laterally supports a pair of monocular scopes formed of laterally disposed sight tubes 270 which distally support eye pieces. Magnification lenses are mounted in the sight tubes 270 to provide a magnification power from about 20 to 100, preferably about 50. The undersurface of the scope member 148 has a foot 274 which rests on the stage member 158 and provides the correct vertical separation for calibration of the dial indicators. At the factory calibration setting, the foot 274 of the scope member is separated from the stage member by a predetermined distance, typically 0.025 inch, which is half the range of displacement of the dial indicators. At this calibrated position, the magnification lenses of the scopes will be focused on the cross hair targets 220 (see FIG. 21).

The body 147 of the scope member 148 also has a pair of L-shaped lugs 242 and 243 which extend from its front surface 143, normal to the angled front surfaces 131 and 133 of the plate 152. Another lug 245 is provided on the left side 145 of the body 147. These lugs provide extensions which ride on the cams 226, 228 and 230 (see FIG. 17).

Referring now to FIG. 26, the targets 220 on the stage member are a pair of crossed lines, preferably with a dot 284 at their intersection. A short line 287 is provided as an extension of each end of the crossed lines 280 and 282. Within each of the quadrants 286 formed by the crossed lines is located half of a vernier scale (stage scale 288) that comprises ten lines spaced apart at 0.001 inch increments. Preferably an indica 290 comprising a circle with a diagonal slash is also located at a precise position relative to each of the stage scales 288. The stage scales 288 in diagonal quadrants are aligned parallel to each other, and perpendicular to the stage scales in the other quadrants.

Each of the scopes is provided with a reticle 292 in its field of view, which is shown in FIG. 27. The reticle 292 has two rows, 294 and 296, of calibration lines which are spaced apart at 0.001 inch increments. The rows are perpendicular and correspond to the crossed lines of the stage indica. Each of the quadrants 298 formed by the crossed rows 294 and 296 has a second half of a vernier scale (scope scale 300), comprising eight lines spaced apart at 0.0009 inch.

The overlay of the reticle 292 and target 220 is shown in FIG. 28. The crossed lines are aligned with the crossed rows of spaced-apart calibration marks, and the scope and stage scales in combination form a vernier scale 302 which permits accurate calibration to 0.0001 inch. The pointer indica 291 cooperate with each vernier scale, and when a pointer indica 291 is directed to an indica 290 it indicates to the user that the correct vernier scale is in the diagonally opposite quadrant.

The overlay shown in FIG. 28 is in precise center with the dot 284 of the target centered in the circle 285 of the reticle, and with the vernier scales indicated 0.0000, i.e., no misalignment of the scope relative to the stage. In this position, each of the dots 304 and 306 are located at the ends of the line extensions 287.

When there is misalignment, the inspection members can be moved back into alignment by loosening the screws 178 which secure the upper base plate 150 to the upper frame member 44 of the articulator (see FIG. 3). The adjustment knobs 234 of the positioning fixture 158 can then be rotated causing the cams 226, 228 and 230 to realign the upper half to the lower half of the inspection apparatus (see also FIG. 17). Once the precise x-y axis alignment is achieved, screws 178 are tightened to secure the upper plate 150 in a precise orientation on frame member 44 relative to the lower plate 150 on the lower frame member 10 of the articulator. Thereafter, upper and lower dental casts such as cast 153 shown in FIG. 12 can be loaded in the articulator and these casts will be precisely aligned, so that the casts can be removed and interchanged with other articulators which have been calibrated.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. In a calibration device for precision calibration and setting of a dental articulator having upper and lower frames hinged together along a condylar axis at their posteriors by left and right hinges and anterior vertical spacing means at its anterior, thereby establishing right and left axes of rotation extending from a predetermined anterior point and each of said right and left condyles and attachment means to support dental casts at the mid-portions of said frames, wherein the calibration device has a stage member which is removably securable to said articulator lower frame and a scope member removably securable to said articulator upper frame and including a pair of indicators having sensing probes carried at the opposite sides of one of said stage and scope members to indicate the vertical relationships of said stage and scope members, the improvement comprising:

right and left lever means, each pivotally carried by the said one of said stage and scope members and extending from operative contact with the sensing probe of its respective indicator to contact against the other of said members at a point located on a respective right and left axis of rotation.

2. The calibration device of claim 1 wherein said anterior vertical spacing means of said dental articulator comprises an incisal pin carried on said upper frame and an incisal pin rest carried on said lower frame, and said calibration device includes a gage pin of predetermined height which is removably secured between selected anterior locations of said upper and lower frames.

3. The calibration device of claim 1 wherein said stage member has a planar top with laterally extending wings, and wherein each of said indicators is distally mounted on a respective wing of said stage member.

4. The calibration device of claim 3 wherein each of said wings has a distal upright bracket and wherein each of said indicators is secured to a respective bracket with its sensing probe extending downwardly and terminating adjacent said planar top of said stage member.

5. The calibration device of claim 4 including right and left grooves in the planar top of said stage member, each groove extending medially from a location beneath the sensing probe of its respective right and left indicator to a location immediately beneath its respective right and left rotation axis.

6. The calibration device of claim 5 wherein said lever means is received in each of said grooves and is secured therein by a pivot pin which is seated in said calibration stage member.

7. The calibration device of claim 1 wherein said stage member supports a mounting plate on its under surface.

8. The calibration device of claim 1 wherein said scope member has a mounting plate secured to its upper surface.

9. The calibration device of claim 1 including right and left magnification means positioned at right and left lateral locations on said scope member.

10. The calibration device of claim 9 wherein said magnification means comprise left and right monocular scopes.

11. The calibration device of claim 10 wherein each of said scopes comprises a tubular housing with objective and eyepiece lenses.

12. The calibration device of claim 11 wherein each of said scopes includes reticle means.

13. The calibration device of claim 12 including target means carried on the flat planar surface of said stage member, one each immediately below a respective magnification means.

14. The calibration device of claim 13 wherein each of said reticle and target means have cooperating indica to provide a vernier scale registering relative positions of said stage and scope members.

15. The calibration device of claim 14 wherein said target includes a cross-hair indica dividing said target into equal sectors and including first half vernier scales in at least one of said sectors.

16. The calibration device of claim 15 wherein said reticle means includes a pair of scales, one each aligned with a respective one of said cross-hair indica of said stage member and dividing said reticle means into equal sectors, and including second half vernier scale means located in at least one of said sectors to align with a respective one of said first vernier scale means.

17. The calibration device of claim 16 wherein said target sectors are quadrants, and including four sets of said first half vernier scale means, arranged one each in each of said quadrants of said target, and corresponding four sets of second half vernier scales arranged one each in each of said quadrants of said reticle means.

18. The calibration device of claim 13 including a dot and circle, one of which is centered in said reticle and the other of which is centered on said target for mutual alignment when said stage and scope members are in centric.

19. In a calibration device for precision calibration and setting of a dental articulator having upper and lower frames hinged together along a condylar axis at their posteriors by left and right hinges and anterior vertical spacing means at its anterior and attachment means to support dental casts at their mid-portions, wherein the calibration device has a stage member which is removably securable to said articulator lower frame and a scope member removably securable to said articulator upper frame and including right and left monocular scopes positioned at right and left lateral locations on said scope member, the improvement comprising:

a. reticle means in each of said monocular scopes;
b. target means carried on a flat planar surface of said stage member, one each immediately below a respective monocular scope; and
c. cooperating first and second indica, one each in said reticle and target means to provide a vernier scale which registers relative positions of said stage and scope calibration members.

20. The calibration device of claim 19 wherein said monocular scopes comprise tubular housings with objective and eyepiece lenses.

21. The calibration device of claim 19 wherein said target means includes a cross-hair indica dividing said target into equal quadrants and including first half vernier scale means in at least one of said quadrants.

22. The calibration device of claim 21 wherein said reticle means includes a pair of orthogonal scales arrayed to lie on said cross-hair indica of said stage member and dividing said reticle means into quadrants, and including second half vernier scale means located in at least one of said quadrants to align with said first half vernier scale means.

23. The calibration device of claim 22 including four sets of said first half vernier scale means, arranged one each in each of said quadrants of said target means, and corresponding four sets of second half vernier scales arranged one each in each of said quadrants of said reticle means.

24. The calibration device of claim 23 including a dot and circle, one of which is centered in said reticle means and the other of which is centered on said target means for mutual alignment when said stage and scope members are in centric alignment.

* * * * *